(12) United States Patent  
Moulder et al.

(10) Patent No.: US 9,020,584 B2  
(45) Date of Patent: Apr. 28, 2015

(54) METHOD FOR THE DETECTION OF SUBCUTANOUS CARDIAC SIGNALS AND A CARDIAC DEVICE FOR USE IN DETECTING SUBCUTANEOUS CARDIAC SIGNALS

(71) Applicant: Biotronik SE & Co. KG, Berlin (DE)

(72) Inventors: J. Christopher Moulder, Portland, OR (US); Christopher S. de Voir, Tigard, OR (US); R. Hollis Whittington, Portland, OR (US); Garth Garner, Tigard, OR (US)

(73) Assignee: Biotronik SE & Co. KG, Berlin (DE)

( * ) Notice: Subject to any disclaimer, the term of this patent is extended or adjusted under 35 U.S.C. 154(b) by 0 days.

(21) Appl. No.: 14/181,411

(22) Filed: Feb. 14, 2014

(65) Prior Publication Data

US 2014/0236034 A1   Aug. 21, 2014

Related U.S. Application Data

(60) Provisional application No. 61/766,137, filed on Feb. 19, 2013.

(51) Int. Cl.
*A61B 5/04* (2006.01)
*A61B 5/0472* (2006.01)
*A61B 5/00* (2006.01)

(52) U.S. Cl.
CPC ............. *A61B 5/0472* (2013.01); *A61B 5/7203* (2013.01)

(58) Field of Classification Search
CPC . A61N 1/3704; A61N 1/3943; A61B 5/7203; A61B 5/0452; A61B 5/0468
See application file for complete search history.

(56) References Cited

U.S. PATENT DOCUMENTS

| 4,458,692 | A | 7/1984 | Simson |
| 5,967,994 | A | 10/1999 | Wang |
| 2007/0276447 | A1* | 11/2007 | Sanghera et al. ............... 607/32 |

OTHER PUBLICATIONS

European Search Report issued for EP Appl. No. 14153174.9, dated Apr. 10, 2014, 6 pages.

* cited by examiner

*Primary Examiner* — Robert N Wieland
(74) *Attorney, Agent, or Firm* — ARC IP Law, PC; Joseph J. Mayo (57) ABSTRACT

A cardiac device and method for detecting QRS signals within a composite heart signal of a body including providing at least two input heart signals via at least two separate input channels, wherein each of the at least two input heart signals is recorded by pairs of sensing electrodes that have one electrode in common and provided coincidental in time. The cardiac device and method include generating estimated signals from the input heart signals, combining the input heart signals and the estimated signals to a combined input stream (SECG), and detecting the QRS signal by comparing the combined input stream (SECG) to an adaptive detection threshold (ATHR) which adapts throughout time.

22 Claims, 8 Drawing Sheets

METHOD FOR THE DETECTION OF SUBCUTANOUS CARDIAC SIGNALS AND A CARDIAC DEVICE FOR USE IN DETECTING SUBCUTANEOUS CARDIAC SIGNALS

This application claims the benefit of U.S. Provisional Patent Application 61/766,137, filed on 19 Feb. 2013, the specification of which is hereby incorporated herein by reference.

BACKGROUND OF THE INVENTION

1. Field of the Invention

At least one embodiment of the invention relates to the sensing of electrocardiogram (ECG) signals, in particular to the sensing of subcutaneous ECG signals.

2. Description of the Related Art

A QRS complex is a specific sequence of deflections that may be detected within an electrocardiogram (ECG) signal, measured from the body of a living being. It generally represents the depolarization of the right and left ventricles of the heart. Typically, an ECG signal shows five deflections, or waves, that are arbitrarily named P, Q, R, S and T. In an ECG signal, Q waves are generally represented as small downward deflections following the P wave, and the R wave is generally represented as a large upward deflection, or as a spike. The S wave generally represents a small downward deflection following the R wave. The time intervals between QRS complexes typically indicate the heart rate of the heart of a living being. The QRS complex of a healthy human being generally lasts for a time interval between 60 to 120 milliseconds. Wide QRS complexes, or those lasting longer than 120 milliseconds, typically indicate ventricle impairment such as bundle branch blocks. Furthermore, often, with bundle branch blocks, a second upward deflection occurs within the QRS complex. Other causes for a wide QRS complex include ectopic foci or abnormal pacemaker sites that slow conduction within the heart and increase the depolarization time of the heart muscle. Moreover, other deviations of a patients QRS complex from a normal one may indicate various symptoms for diseases or malfunctions of different parts or areas of, for example, a human heart.

It has been a central issue of cardiac research to enable precise detection, analysis, and evaluation of a patient's QRS complex. Therefore, there is a need for a method that enables a highly accurate detection of a QRS complex with an increased signal-to-noise (SNR) ratio, compared to methods disclosed within the state of the art.

BRIEF SUMMARY OF THE INVENTION

According to at least one embodiment of the invention, a method for the detection of QRS signals sensed by pairs of electrodes is provided. The method may include the step of providing at least two input heart signals via at least two separate input channels, with each channel connected to external sensing electrodes, wherein each of the at least two input heart signals may be recorded by pairs of sensing electrodes that have one electrode in common and provided coincidental in time. In at least one embodiment, the method may include one or more of generating estimated signals from the input heart signals, combining the estimated signals to a combined input stream, and detecting the QRS signal by comparing the combined input stream to an adaptive detection threshold that may adapt throughout time. The estimated signals, in at least one embodiment, may include spatially derived estimates and/or temporally derived estimates.

According to one or more embodiments, an advantage of the method provided may include the use of spatial and temporal estimates for the combination of input heart signals provided by different input channels, wherein the signal to noise ratio may be increased by smoothing at least some of the random noise associated with each input channel, while emphasizing the QRS complexes measured from the combined input stream. In at least one embodiment, the method may be particularly advantageous when one electrode of the pairs of sensing electrodes is shared by two of the input channels. Moreover, via the adaptation of the adaptive detection threshold, in one or more embodiments, the detection criteria for the detection of a QRS complex may be adjusted to the behavioral characteristics of the heart of a living being.

In at least one embodiment of the invention, the temporally derived estimate for an input channel may be calculated as a smoothed value calculated from samples of the input heart signal of an input channel. In one or more embodiments, an average value may be calculated using samples of the input heart signal of an input channel that may be taken before and after a current sample of the input heart signal of the respective input channel. In such embodiments, random noise may be smoothened in each of the input channels.

In one or more embodiments, the spatially derived estimate of an input channel may be calculated as a combination of the input heart signals provided by the other input channel(s).

The calculation of the spatially derived estimates, according to at least one embodiment, may be calculated since for these at least two input channels, the heart signals may be gathered by pairs of sensing electrodes for each channel, where any two channels may share one electrode. In at least one embodiment, a spatially derived estimate of any input channel may be made from the at least two input channels, thereby reducing the influence of local electrode noise.

Preferably, in one or more embodiments, the step of combining the estimated signals to a combined input stream may include the step of combining one or more of the spatially derived estimate, the temporally derived estimate and optionally the input heart signal of an input channel for each input channel respectively, to provide a composite estimate signal for each input channel respectively.

To reduce the probability that the combining may produce a null result, according to one or more embodiments, one composite channel may be augmented before the final combination. In at least one embodiment, a prospect may be calculated for each of the input channels respectively, using the composite estimate signals, wherein within the calculation of a certain prospect for a channel, the respective composite estimate signal calculated for the respective channel may be augmented.

The concept of prospect, in at least one embodiment, enables for the selection of at least one prospect from the combined input streams according to selectable criteria, such as one or more of peak or maximum signal amplitude and signal-to-noise ratio.

In at least one embodiment, the maximum signal amplitude of the prospect may be the selection criteria.

In one or more embodiments, the at least two input heart signals or the combined input stream, or both, may be filtered with a high-pass, low-pass, or a pass-through filter, or any combination thereof. In at least one embodiment, at least two filters may be arranged in series or at least two filters may form a filter loop structure. In at least one embodiment, the net pass band output by the filters arranged in series or by the at least two filters that form a filter loop structure may be between 1 and 50 Hz.

By way of one or more embodiment of the invention, the adaptive detection threshold may be set after each detection of a QRS signal, wherein the value of the adaptive detection threshold may be initially set as a percentage of a QRS-peak amplitude of the combined input stream measured during a sensing cycle, wherein the value of the adaptive detection threshold may be initially set as a different percentage of a QRS-peak amplitude of the combined input stream measured during a detection of a QRS signal, and wherein the adaptive detection threshold may decrease throughout time.

In at least one embodiment of the invention, the adaptive detection threshold may decrease in steps, for example by an absolute, relative, or adaptive value until it reaches a target threshold. As such, in one or more embodiments, the value of the target threshold may be initially set as a percentage of a QRS-peak amplitude of the combined input stream measured during a detection of a QRS signal, and the adaptive detection threshold and the target threshold are greater than or equal to a minimum threshold. In one or more embodiments, the adaptive detection threshold and the target threshold may be adjusted for every QRS-peak detected, which significantly increases detection accuracy.

By way of one or more embodiments, the duration of a step may be adjusted based on a moving average of the ventricular cycle length measured from the composed heart signal of the body from which the combined input stream may be measured. In at least one embodiment, the adaptive detection threshold or the target threshold may be controlled, such that they may remain above the minimum threshold, since the steps may be adjusted such that the target threshold may be above or equal to the minimum threshold. Adjusting the threshold decay, in one or more embodiments, may also prevent noise detection by maintaining the detection threshold as high as possible. The detection threshold, in at least one embodiment, may be adjusted to detect the next expected QRS complex while avoiding noise between the complexes, such as the T-wave.

In one or more embodiments of the invention, the adaptive detection threshold may be set to the minimum threshold based on the last detected QRS complex after a predetermined time. In at least one embodiment, QRS-peaks with a low amplitude may be detected, which may allow for a precise analyses of the heartbeat characteristics of a living being.

According to at least one embodiment, the minimum threshold may be determined by a vector residual of the composite estimate signals. In at least one embodiment, an error $\epsilon$ may be calculated, filtered and used for the determination of the minimum threshold. The calculation of error $\epsilon$, in one or more embodiments, may depend on the arrangement of the electrodes and which electrode may be the reference for each channel. Error $\epsilon$, in at least one embodiment, may be calculated wherein it is zero if no noise is present and a value greater than zero may represent the noise floor. In at least one embodiment, $\epsilon$ may be equal to $\epsilon = A_{est} - B_{est} - C_{est}$. In one or more embodiments, the minimum threshold may dynamically depend on the composite estimate signals. By setting the minimum threshold to a vector residual equal to a noise error, in at least one embodiment, it may be assured that only QRS-peaks with amplitudes greater than the noise error are detected.

In one or more embodiments of the invention, a low signal flag (LSF) may be set if a QRS-peak amplitude of the combined input stream, which may be measured during a detection of a QRS signal, may be lower than a scaled value of the minimum threshold. In at least one embodiment, a low signal flag may be set or declared when the peak of a detected QRS complex may be too low to be considered reliable, which may occur if the QRS complex may have low amplitude, noise may have a large amplitude, or if noise may have caused the detection. As such, in one or more embodiments, the reliability of the method is increased.

Furthermore, in one or more embodiments of the invention, a cardiac device for use in detecting QRS signals within a composite heart signal of a body may be provided, and may include an input unit to which at least three external sensing electrodes may be attachable to provide at least two input heart signals recorded by pairs of sensing electrodes via at least two separate input channels provided coincidental in time. In at least one embodiment, the cardiac device may include one or more of an estimation unit that may generate estimated signals from the input heart signals, a combination unit that may combine the three input heart signals and the estimated signals to a combined input stream, an automatic sense control unit that may compare the combined input stream to an adaptive detection threshold that may adapt throughout time, and a system adjustment unit that may adjust at least one parameter of the automatic sense control unit. The cardiac device, in at lest one embodiment, may execute the method according to the invention. With such a cardiac device, in one or more embodiments, the method may be used within a cardiac device, such that the advantages mentioned for the method may also apply to the cardiac device. In at least one embodiment, the system adjustment unit may adjust parameters related to one or more of sensing, noise and timing of the automatic sense control unit.

According to one or more embodiments of the invention, one or more of the estimation unit, the combination unit, the automatic sense control unit, and the system adjustment unit may be included within a digital signal processor. In at least one embodiment, a large variety of applications within a compact digital signal processor or a digital signal processing unit may be implemented.

BRIEF DESCRIPTION OF THE DRAWINGS

The above and other aspects, features and advantages of at least one embodiment of the invention will be more apparent from the following more particular description thereof, presented in conjunction with the following drawings wherein.

DETAILED DESCRIPTION OF THE INVENTION

The following description is of the best mode presently contemplated for carrying out at least one embodiment of the invention. This description is not to be taken in a limiting sense, but is made merely for the purpose of describing the general principles of the invention. The scope of the invention should be determined with reference to the claims.

Figure 1:
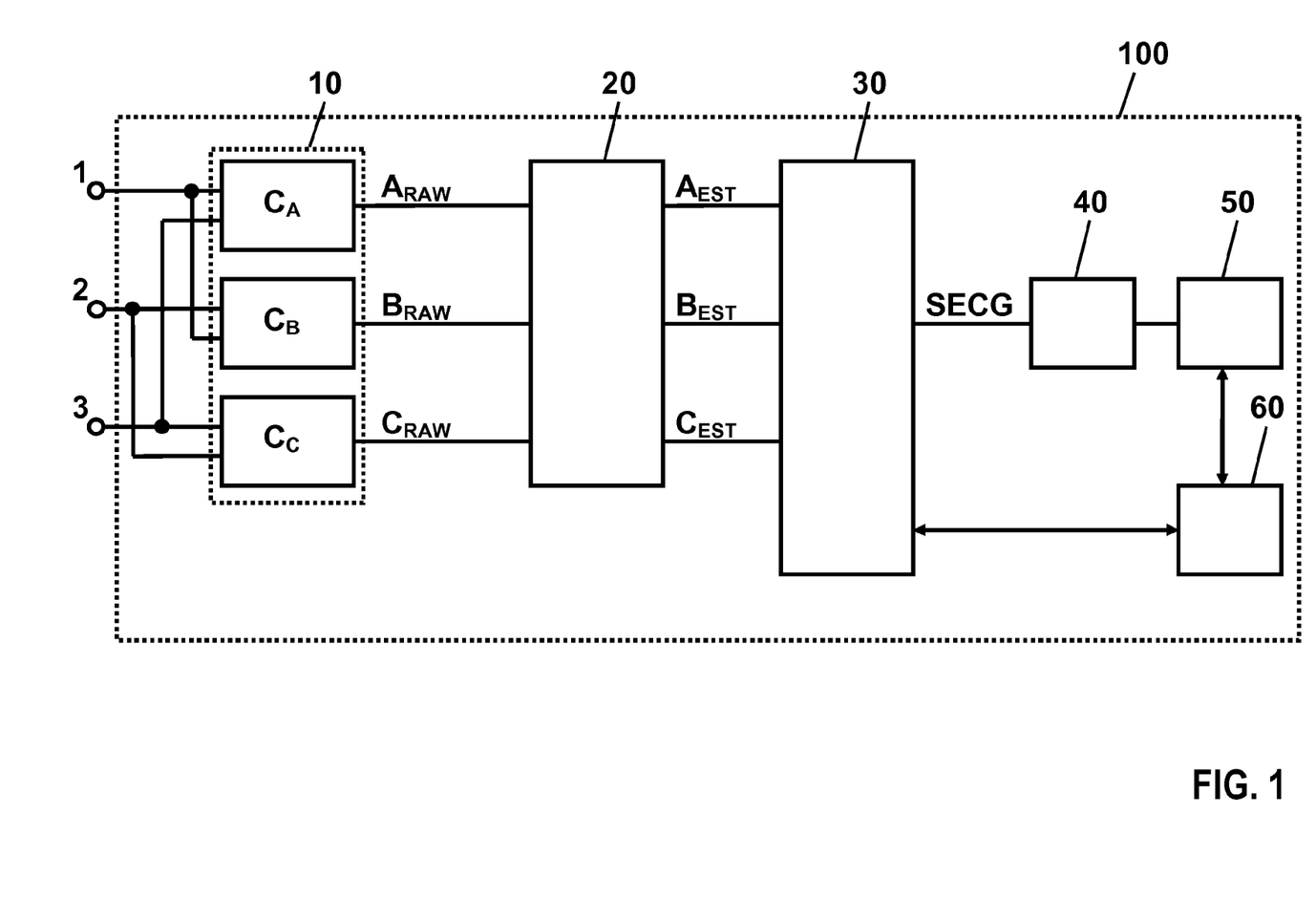
FIG. 1 shows a high level block diagram of a cardiac device and a corresponding method, according to at least one embodiment of the invention.

FIG. 1 shows a high level block diagram of a cardiac device 100 according to at least one embodiment of the invention. A method may be executed by at least one embodiment of the cardiac device 100. The device and associated method, in one or more embodiments, may be designed to make use of at least two sensing vectors in order to increase noise immunity and signal detection accuracy.

The implantable medical device 100, in at least one embodiment, may record the electrical activity of the heart using at least three electrodes that may be placed on the housing of the device. The device in one or more embodiments may be implanted subcutaneously.

Referring to FIG. 1, according to at least one embodiment of the invention, the implantable medical device 100 may include an input unit 10 that may be connected to the electrodes 1, 2 and 3. In one or more embodiments, pairs of the electrodes 1, 2 and 3 may be connected to the input channels $C_A$, $C_B$ and $C_C$. Such input units, in at least one embodiment, may include amplifiers and analog-digital converters. At the output of the input unit 10, in one or more embodiments, three input heart signals $A_{raw}$, $B_{raw}$ and $C_{raw}$ may be provided coincidental in time.

By way of at least one embodiment, in the input unit 10 the input channels $C_A$, $C_B$ and $C_C$ may optionally include signal filtering in hardware or software. For example, in one or more embodiment, the signals may be filtered with a high-pass first order analog Butterworth filter that may provide a corner frequency of 1 Hz. Subsequently, in at least one embodiment, all input channels $C_A$, $C_B$ and $C_C$ may be optionally filtered with a low-pass filter that may provide a corner frequency at 50 Hz to remove any high frequency noise.

In one or more embodiments of the invention, the input heart signals $A_{raw}$, $B_{raw}$ and $C_{raw}$ may be input to an estimation unit 20 that may generate estimated signals from the input heart signals $A_{raw}$, $B_{raw}$ and $C_{raw}$. The estimated signals, in at least one embodiment, may include temporally derived estimates, spatially derived estimates or combinations thereof.

In at least one embodiment, the estimation unit 20 may calculate temporally derived estimates $A_{temporal}$, $B_{temporal}$ and $C_{temporal}$ for each input channel $C_A$, $C_B$ and $C_C$. The temporally derived estimates $A_{temporal}$, $B_{temporal}$ and $C_{temporal}$ may be each equal to an average value calculated from samples of the respective input heart signal $A_{raw}$, $B_{raw}$ and $C_{raw}$ of an input channel $C_A$, $C_B$ and $C_C$, taken before and after a current sample of the input heart signal $A_{raw}$, $B_{raw}$ and $C_{raw}$ of the respective channel $C_A$, $C_B$ and $C_C$ was taken, according to one or more embodiments of the invention. Expressed in other words, in at least one embodiment, the calculation of a temporally derived estimate $A_{temporal}$, $B_{temporal}$ and $C_{temporal}$ may be performed by an averaging filter with no memory that removes some high frequency noise. In one or more embodiments, the temporally derived estimate $A_{temporal}$, $B_{temporal}$ and $C_{temporal}$ may use samples before and after the current sample to produce an average value. This average value, in at least one embodiment, may be the predicted value of the sample in time, which may be calculated for example by the following equation:

$$y[n-1] = \frac{x[n] + x[n-2]}{2},$$

wherein y[n-1] is the temporal estimate of a single input channel delayed by one sample, x[n] is the current sample and x[n-2] is a previous sample delayed by two while n is the relative sample number. In one or more embodiments, the effect of this operation may delay the output by 1 sample. Alternatively, in at least one embodiment, the average value may be calculated using more samples, a moving average filter, or by other functions such as the CDF(2,2) wavelet smoothing function for example.

By way of one or more embodiments, the estimation unit 20 may also calculate the spatially derived estimate of an input channel as the combination of the input heart signals provided by the other input channels. For example, in at least one embodiment, for three input heart signals $A_{raw}$, $B_{raw}$ and $C_{raw}$, using the electrode arrangement as shown in FIG. 2, the spatially derived estimates $A_{spatial}$, $B_{spatial}$, and $C_{spatial}$ may be calculated according to the following equations:

$$A_{spatial} = B_{raw} + C_{raw}$$

$$B_{spatial} = A_{raw} - C_{raw}$$

$$C_{spatial} = A_{raw} - B_{raw}$$

Expressed in other words, in at least one embodiment, the calculation of the spatially derived estimate $A_{spatial}$, $B_{spatial}$, and $C_{spatial}$ may be possible because the input channels or sensing vectors may use common electrodes. Spatially derived estimates, in one or more embodiments, may reduce the influence of local electrode noise by creating an alternate representation of the cardiac vector. In at least one embodiment, each spatially derived estimate $A_{spatial}$, $B_{spatial}$, and $C_{spatial}$ may use two of the raw input channels to estimate using vector mathematics. The spatially derived estimate, in one or more embodiments, may operate on the n-1 sample to maintain timing with the temporally derived estimate. The result predicts the value of, for example in at least one embodiment, the third input channel $C_C$ based on what may be sensed at the first and second input channels $C_A$ and $C_B$.

In one or more embodiments of the invention, the temporal and spatial estimate calculations may be combined. For example, in at least one embodiment, a spatial estimate may be derived from the temporal estimates. Likewise, in one or more embodiments, a temporal estimate may be derived from spatial estimates.

According to at least one embodiment of the invention, the estimation unit 10 may also calculate from the spatially derived estimate, the temporally derived estimate, and the raw input heart signal of an input channel, respectively, a composite estimate signal $A_{est}$, $B_{est}$, and $C_{est}$, respectively. Expressed in other words, in one or more embodiments, a new filtered estimate of each input channel $C_A$, $C_B$ and $C_C$ may be composed of the respective (raw) input heart signals $A_{raw}$, $B_{raw}$ and $C_{raw}$, the temporally derived estimates $A_{temporal}$, $B_{temporal}$, and $C_{temporal}$, and the spatially derived estimates $A_{spatial}$, $B_{spatial}$, and $C_{spatial}$. The following equation, in at least one embodiment, shows how the estimates and the raw data may be combined into the composite estimate signal $A_{est}$, $B_{est}$ and $C_{est}$ for each input channel $C_A$, $C_B$, and $C_C$, respectively:

$$A_{est}=A_{raw}+A_{temporal}+A_{spatial}$$

$$B_{est}=B_{raw}+B_{temporal}+B_{spatial}$$

$$C_{est}=C_{raw}+C_{temporal}+C_{spatial}$$

Combining the three (raw) input heart signals with their estimates, in at least one embodiment, may help to reduce random noise and to increase the signal-to-noise ratio.

In one or more embodiments of the invention, the implantable medical device 100 may include a combination unit 30 that may combine the three composite estimates to form a combined SECG output. To reduce the probability that the combining may produce a null result, in at least one embodiment, one estimate channel may be augmented before the final combination. In at least one embodiment, a prospect $P_A$, $P_B$, and $P_C$ may be calculated for each of the input channels $C_A$, $C_B$, and $C_C$ respectively, using the composite estimate signals $A_{est}$, $B_{est}$, and $C_{est}$, wherein within the calculation of a certain prospect $P_A$, $P_B$ and $P_C$ for an input channel the respective composite estimate signal may be augmented by doubling. For example, in one or more embodiments, the calculation of the prospects $P_A$, $P_B$ and $P_C$ may be performed according to the following equations:

$$P_A=2A_{est}+B_{est}+C_{est}$$

$$P_B=A_{est}+2B_{est}+C_{est}$$

$$P_C=A_{est}+B_{est}+2C_{est}$$

According to at least one embodiment, $P_A$, $P_B$, and $P_C$ may be the prospects and $A_{est}$, $B_{est}$, $C_{est}$ may be the composite estimate signals of the input channels $C_A$, $C_B$, and $C_C$, respectively. In at least one embodiment of the invention, all three prospects are produced simultaneously.

By way of one or more embodiments of the invention, the concept of prospect may allow for the selection of at least one prospect as the best suited combined input stream SECG according to selectable criteria such as peak or maximum signal amplitude or signal-to-noise ratio.

In at least one embodiment, the selection criterion may be the maximum signal amplitude of the prospect. In at least one embodiment, local and system inherent noise may be reduced significantly.

In one or more embodiments, a hysteresis may be implemented within combination unit 30 in order to reduce the frequency of changing the doubled composite estimate signal, which may distort signal morphology. For example, in at least one embodiment, if after the prospect with $A_{est}$ being doubled is selected as the combined input stream, the prospect with $B_{est}$ doubled may meet the prospect selection criteria, and the prospect with $B_{est}$ doubled may not be immediately used. Rather, in at least one embodiment, prospect with $A_{est}$ being doubled may continue to be used as the combined input stream unless the next QRS detection determines the prospect with $B_{est}$ doubled also meets the prospect selection criteria. At that point, in one or more embodiments, the prospect with $B_{est}$ doubled may be used as the combined SECG input stream. In at least one embodiment, the chosen prospect may change only if two consecutive QRS-peak amplitudes lead to the same combined input stream choice.

The combination, in one or more embodiments, may be expressed using the following equation:

$$\text{Combo}=\max(\text{prospect}_A, \text{prospect}_B, \text{prospect}_C).$$

Figure 2A:
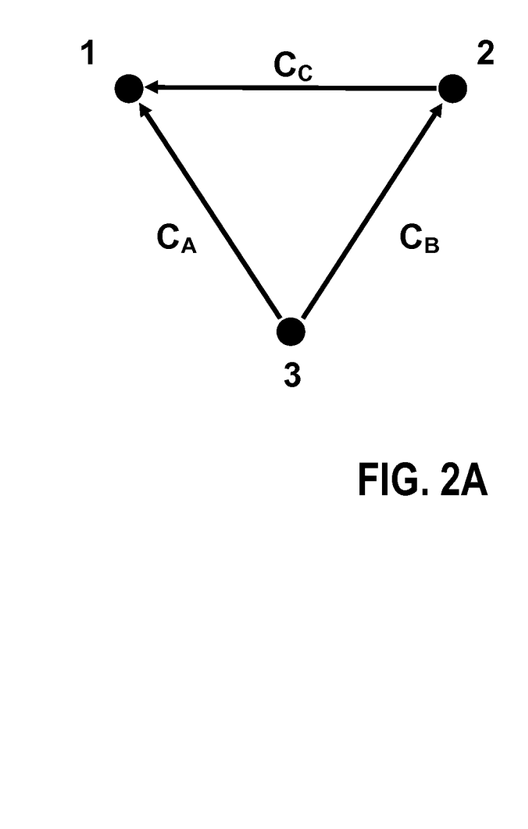
FIGS. 2A & 2B shows input channel orientations of a cardiac device according to at least one embodiment of the invention.
Figure 2B:
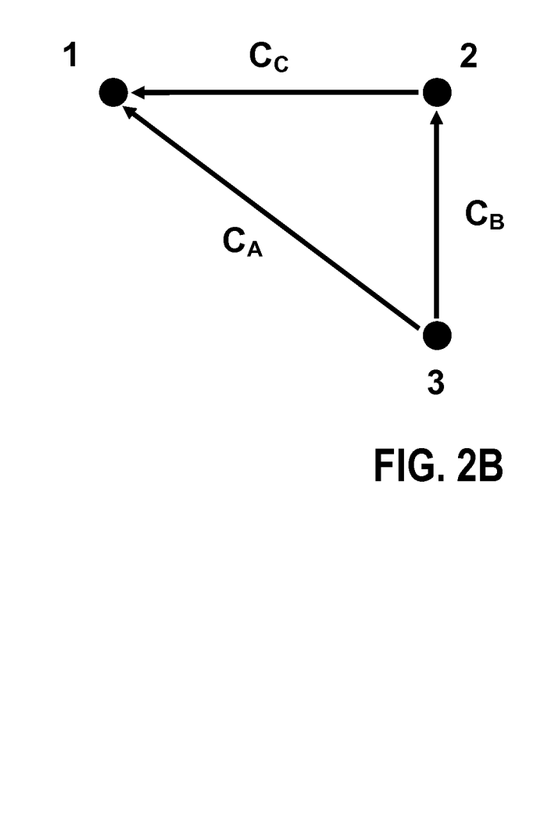

FIG. 2A and FIG. 2B show representations of electrode placements of a cardiac device 100 according to at least one embodiment of the invention. Electrical signals originating from cardiac activity, in at least one embodiment, may be sensed by the electrodes 1, 2 and 3 symbolized by the black circles in FIG. 2A and FIG. 2B. In one or more embodiments, the processing of the electrical signals sensed between two electrodes may be performed, for example for pacemakers with signals sensed by bipolar electrodes implanted in the heart. In at least one embodiment, signals sensed between the various electrode combinations described hereafter may be processed substantially simultaneously. The three electrodes, in one or more embodiments, enable the recording of three input channels, each channel having an electrode in common with each of the other two channels. Referring to FIG. 2A and FIG. 2B, according to at least one embodiment of the invention, signals sensed between electrodes 3 and 1 may be recorded as input channel $C_A$, signals sensed between electrodes 3 and 2 may be recorded as input channel $C_B$, and signals sensed between electrodes 2 and 1 may be recorded as input channel $C_C$. In one or more embodiments of the invention, each of the electrodes may be shared by two input channels. Expressed in other words, in at least one embodiment, the cardiac device 100 may include three input channels $C_A$, $C_B$ and $C_C$ that may receive different projections of the heart signal as input heart signals $A_{raw}$, $B_{raw}$ and $C_{raw}$. In one or more embodiments, each input channel $C_A$, $C_B$ and $C_C$ may use a single pair of the three sensing electrodes and each input channel $C_A$, $C_B$ and $C_C$ may sense a different planar projection of the heart signal, wherein the projections may be coincident in time. In at least one embodiment, noise on each input channel $C_A$, $C_B$ and $C_C$ may be determined, in part, by the local activity around the sensing electrodes in that particular pair. Combining the three input channels $C_A$, $C_B$ and $C_C$ into a single input channel, in one or more embodiments, increases the signal to noise ratio by smoothing some of the random noise associated with each input channel $C_A$, $C_B$ and $C_C$, while emphasizing the QRS-signals, so the QRS complexes.

Figure 3:
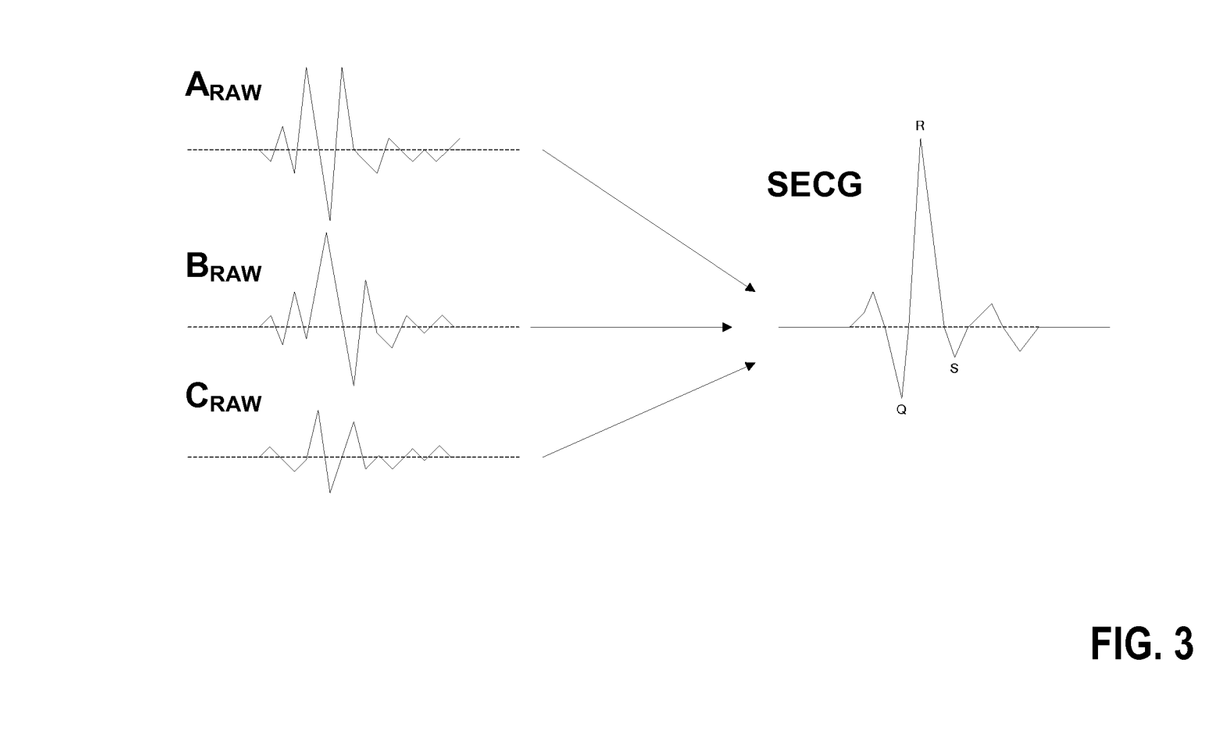
FIG. 3 shows a schematic illustration of the combination of three input heart signals to a combined input stream according to at least one embodiment of the invention.

FIG. 3 shows a schematic illustration of the combination of three input heart signals $A_{raw}$, $B_{raw}$, and $C_{raw}$ to the eventual combined input stream SECG, according to at least one embodiment of the invention. In one or more embodiments, via three different input channels $C_A$, $C_B$ and $C_C$, three input heart signals $A_{raw}$, $B_{raw}$, and $C_{raw}$ may be provided, which in FIG. 3 show three different measurements (planar projections) of the same QRS signal measured from the heart of a living being. In at least one embodiment, the three different input heart signals $A_{raw}$, $B_{raw}$, and $C_{raw}$ may be combined to a single data stream, the combined input stream SECG, via the calculation of spatial and temporal estimates and the prospects, as described above.

Referring back to FIG. 1, by way of one or more embodiments of the invention, the combined input stream may be filtered in an optional filter unit 40 with a high-pass, low-pass, or a pass-through filter, or any combination thereof, before the step of comparing is performed. In at least one embodiment, the combined input stream SECG may be passed through two second order Butterworth filters before being sent to either an automatic sense control unit (ASC) 50 for the detection, or to a memory (not shown) for internal storage. Further filtering of the combined input stream SECG, in at least one embodiment, may remove noise not mitigated by the combination operation performed by the combination unit 30 as already mentioned. In one or more embodiments, filters may each be configured as high-pass, low-pass or pass-through (delay) filters. As shown, in at least one embodiment, the filter parameters may be set by a system adjustment unit 60. In one or more embodiments, the filter parameters may also be stored in a re-programmable area of the cardiac device 100 memory (not shown).

In at least one embodiment of the invention, the filters may be used as a second order low-pass filter and as a second order high-pass filter, each of which may introduce a delay of 2 samples. In one or more embodiments, cardiac devices 100 may be carried out, in which the filters may be programmed as pass-through filters, with possible delays of 0, 1 or 2 samples. In at least one embodiment, the maximum delay of 2 samples may maintain time synchronization between the detection and snapshot versions of the output waveform. The filters, by way of at least one embodiment, may be arranged in series using a filter loop structure. By arranging the filter as a loop, in one or more embodiments, the same hardware may be used to implement each filter, where only the filter coefficients need be changed to enable the type of filter desired. In at least one embodiment, the output of the combination unit 30 may pass through each of the filters. The output of the filter loop, in at least one embodiment, may be sent to either the automatic sense control unit 50 for detection or to a memory (not shown) for internal storage.

In at least embodiment, the filter may output differently filtered signals with one filter parameter set for QRS detection and another filter parameter set for saving and later review. As such, in one or more embodiments, a more faithful reproduction may be viewed by the physician, while a version with very little noise may be used for QRS detection.

According to at least one embodiment of the invention, the combined signal may be input to an automatic sense control unit 50 that is configured to compare the combined input stream (SECG) to an adaptive detection threshold (ATHR), which may adapt throughout time. If the combined input stream (SECG) exceeds the adaptive detection threshold (ATHR), in at least one embodiment, a QRS detection may be indicated and a corresponding marker signal may be generated.

Figure 4:
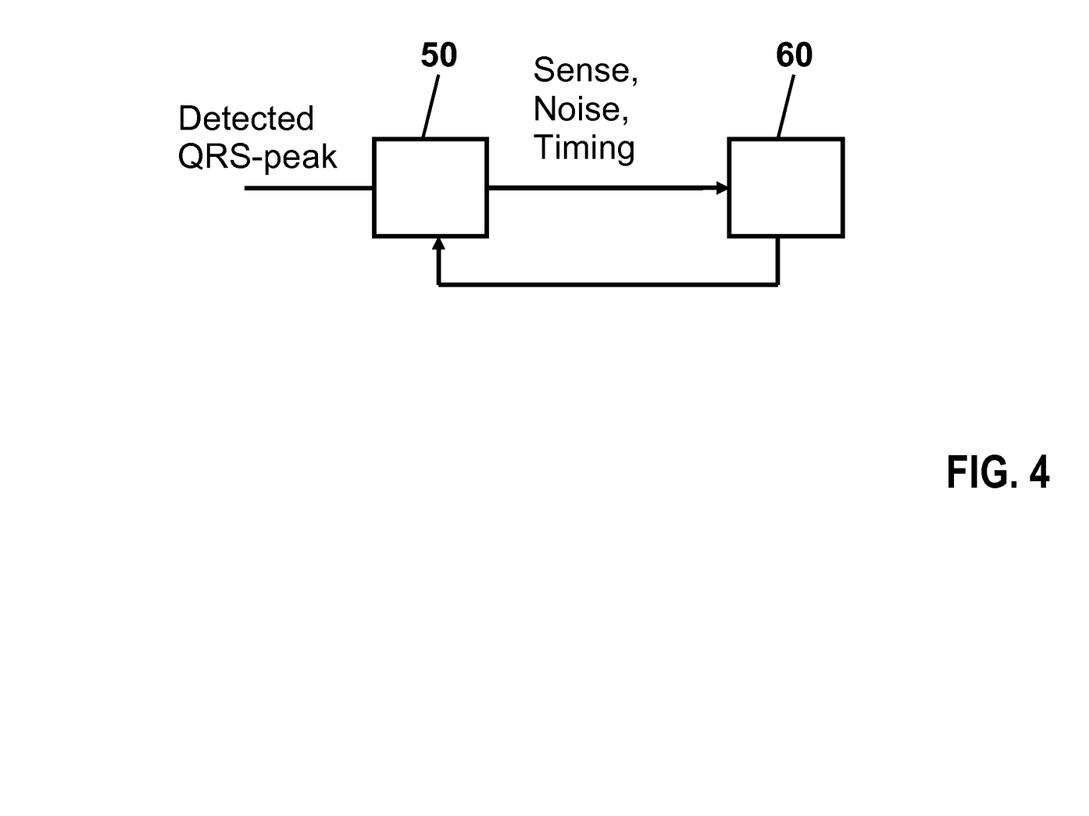
FIG. 4 shows a schematic illustration of the general QRS-peak detection flow according to at least one embodiment of the invention.

FIG. 4 shows a schematic illustration of the general QRS-peak detection flow according to at least one embodiment of the invention. The automatic sense control unit 50 of FIG. 1, shown in more detail in FIG. 4, may output specific information about a detection and noise status, as well as about timing that may be used by the cardiac device 100, according to at least one embodiment of the invention. In at least one embodiment, the cardiac device 100 may include a system adjustment unit 60 which may adjust the parameters of the automatic sense control unit 50 based on a previous detection, especially based on the detection of a previous QRS-peak, noise condition, and/or timing. In at least one embodiment, the outputs from the automatic sense control unit 50 may be returned to the system adjustment unit 60 to control the combination calculations, for example the determination of which prospect to use.

Figure 5:
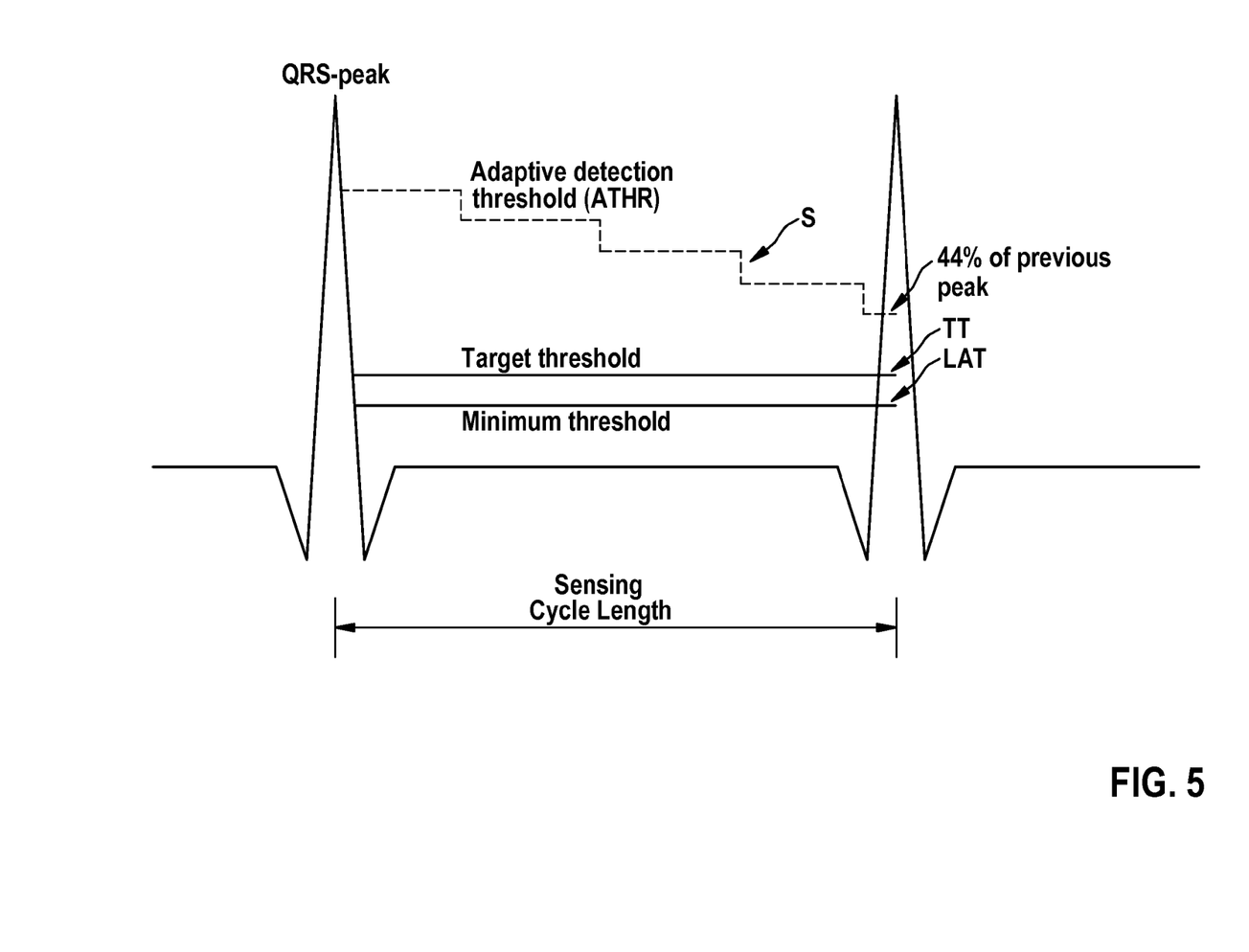
FIG. 5 shows a schematic illustration of a threshold adjustment for large amplitude QRS-peaks according to at least one embodiment of the invention.

FIG. 5 shows a schematic illustration of a threshold adjustment for large amplitude QRS-peaks according to at least one embodiment of the invention. In one or more embodiments, the adaptive detection threshold ATHR may be set after each sensing cycle which may start with the detection of a QRS-complex, wherein the value of the adaptive detection threshold ATHR may be initially set as a percentage of a QRS-peak amplitude of the combined input stream SECG measured during a sensing cycle. In at least one embodiment, the adaptive detection threshold ATHR may decrease in steps S during a sensing cycle, until it reaches a target threshold TT, wherein the value of the target threshold TT may also be initially set as a percentage of a QRS-peak amplitude of the combined input stream SECG measured during a sensing cycle. In one or more embodiments, the adaptive detection threshold ATHR and the target threshold TT may both be greater than or equal to a minimum threshold LAT, and may be set to different percentage values of the QRS-peak amplitude. Expressed in other words, in at least one embodiment, after each detection, the adaptive detection threshold ATHR may be set based on the amplitude of the QRS-peak detected within a combined input stream SECG. By way of one or more embodiments, the adaptive detection threshold ATHR may decay in steps S, which may be determined by a step duration and a step size, until it reaches the target threshold TT, which may also be based on the QRS-peak amplitude. The adaptive detection threshold ATHR and the target threshold TT, in at least one embodiment, may not be lower than the minimum threshold LAT. The adaptive detection threshold ATHR, in one or more embodiments, may not decrease beyond the target threshold TT. Furthermore, in at least one embodiment, the duration of a step S may be adjusted based on a moving average of the ventricular cycle length measured from the composite heart signal SECG of a patient. The adaptive detection threshold ATHR steps S may be set, such that the ATHR may reach a set amplitude at a point in time when the next QRS peak is expected. In this way, in one or more embodiments, the threshold may be maintained above the noise floor as long as possible, such that only QRS complexes may be detected. In FIG. 5, in one or more embodiments of the invention, the adaptive detection threshold ATHR may be initially set equal to an amount of 75% of the QRS-peak amplitude shown on the left side of FIG. 5. In this example, in at least one embodiment, after the time of a sensing cycle length has passed, the amount of the adaptive detection threshold ATHR may have decreased to a value that is equal to 44% of the amount of the previous QRS-peak amplitude.

Figure 6:
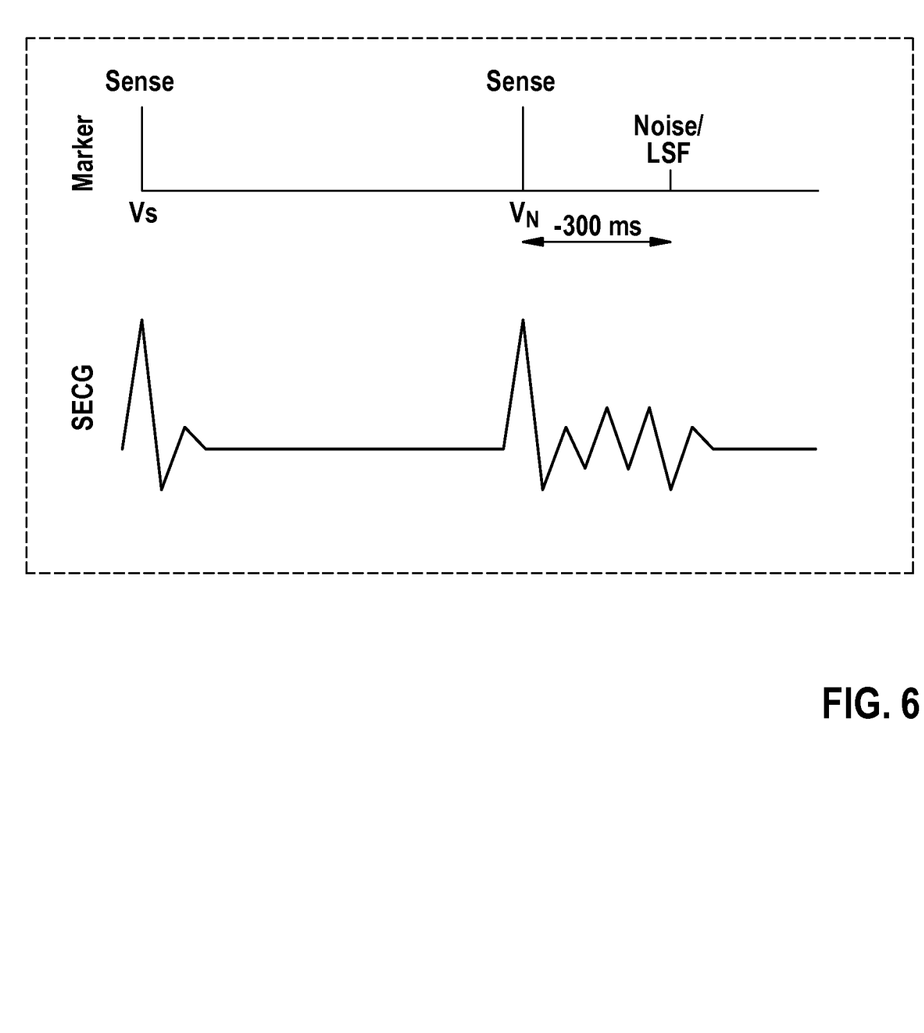
FIG. 6 shows a timing diagram for sense and noise markers settable by the cardiac device and a combined input stream showing a QRS complex without noise followed by a QRS complex with noise, according to at least one embodiment of the invention.

FIG. 6 shows a timing diagram for sense and noise markers settable by the cardiac device 100 and a combined input stream SECG showing a QRS complex without noise followed by a QRS complex with noise, according to at least one embodiment of the invention. In one or more embodiments, noise conditions may occur only after a sensed event. While the timing diagram is shown in the upper area of FIG. 6, the combined input stream SECG is shown in the lower area of FIG. 6. According to at least one embodiment, a sense marker may be generated when the adaptive detection threshold ATHR may be crossed by the combined input stream SECG, which may be detected as a valid sensed event Vs and which may be seen on the left side of the upper diagram of FIG. 6. On the left side in the lower diagram of FIG. 6, the corresponding QRS-peak within the combined input stream SECG is shown, which may have led to the detection of the valid sensed event Vs, in at least one embodiment of the invention. On the right side of the upper diagram of FIG. 6, another event may be sensed which may be identified as an invalid sensed event $V_N$ due to noise following a detected QRS-peak, in at least one embodiment of the invention. In one or more embodiments, within a delay of about 300 ms, if a low signal flag LSF or noise flag is set, which will be described further below, the preceding sensed QRS may be determined to be invalid. In at least one embodiment, on the right side of the lower diagram of FIG. 6, a QRS-peak followed by noise may be seen within the combined input stream SECG, which may have led to the setting of the noise marker and the low signal flag LSF. In at least one embodiment, the low signal flag LSF may be available immediately following a detection hold-off period DHP of approximately 300 ms, while the noise flag may be generated within the DHP. In at least one embodiment, if either of the noise markers (noise or low signal flag LSF) may be generated, the preceding sense marker may be invalid. In one or more embodiments, a valid sensed event is identified by Vs, and an invalid sensed event is identified by $V_N$. Likewise, in at least one embodiment, a valid sensed interval does not include a $V_N$ event.

In at least one embodiment of the invention, a sense detection may occur the first time the combined input stream SECG crosses the adaptive detection threshold ATHR. In one or more embodiments, three timers may then be activated: a peak detection window PDW, a detection hold-off period DHP and a noise sense window NSW. In at least one embodiment, a QRS-peak within the combined input stream SECG may be detected during the peak detection window PDW. The nominal settings for this algorithm, in at least one embodiment, may set the peak detection window PDW and the detection hold-off period DHP to the same nominal length. During the PDW, in at least one embodiment, the combined input stream may be sampled and the peak value may be detected. During the DHP, in at least one embodiment, no new events may be sensed and labeled as $V_s$. In one or more embodiments, the NSW may be a retriggerable timer that may be retriggered whenever a threshold crossing occurs after detection of a new QRS event. If a threshold crossing occurs after DHP and while NSW is active, in at least one embodiment, then a noise flag may be triggered and the timer may reset. In one or more embodiments, no new QRS detection may occur as long as the NSW is active.

Referring back to FIG. 5, in at least one embodiment, the adaptive detection threshold ATHR may decay over time until it reaches the target threshold TT. If no new sense detection occurs within a specific time, in at least one embodiment, the adaptive detection threshold ATHR may be set to the current minimum threshold LAT. Expressed differently, in one or more embodiments, the adaptive detection threshold ATHR may be set to the minimum threshold LAT of a current sensing cycle, if no new sensing cycle has begun within a specified time.

As already mentioned, in at least one embodiment of the invention, the adaptive detection threshold ATHR and the target threshold TT may be initially set as a percentage of the previous QRS-peak detected at the end of the peak detection window. In at least one embodiment, the minimum threshold LAT may be calculated and set after every QRS-peak detection, or after each sense time-out STO. In one or more embodiments, if the minimum threshold LAT is calculated and set after the sense time-out STO, then it may not be changed after the QRS-peak detection immediately following sense time-out STO. The minimum threshold LAT, in one or more embodiments, may be calculated and set on subsequent QRS-peak detections and sense time-outs STO.

In at least one embodiment, the minimum threshold LAT may be determined by a vector residual of the composite estimate signals $A_{est}$, $B_{est}$, and $C_{est}$. An error $\epsilon$, which includes different noise components, may be calculated, filtered and used for the determination of the minimum threshold LAT, in at least one embodiment, wherein $\epsilon$ is equal to $\epsilon = A_{est} - B_{est} - C_{est}$. Moreover, in one or more embodiments, the error $\epsilon$ may be smoothed, following the equation $\epsilon_n = \frac{1}{4}|\epsilon_{HP}| + \frac{3}{4}\epsilon_{n-1}$, wherein $\epsilon_{HP}$ is the high-pass filtered error, wherein $\epsilon_{n-1}$ is the error of the previous sample filtered with a moving average filter, and wherein $\epsilon_n$ is used for the determination of the minimum threshold LAT. In at least one embodiment, the error signal $\epsilon$ is expected to be zero when no noise is present. In one or more embodiments, the specific equation to determine $\epsilon$ depends on the arrangement of the three electrodes and which electrode may be the reference for each channel. In at least one embodiment, the determination of the error may follow vector math where the sum of the vectors may be zero. When noise is present, in at least one embodiment, the channels may not be as closely related to each other and so the sum of the vectors is determined as the error.

In at least one embodiment of the invention, a low signal flag LSF may be set if a detected QRS-peak amplitude of the combined input stream SECG, which may be measured during PDW, may be lower than a multiple of the amplitude of the minimum threshold LAT. For example, in one or more embodiments, a low signal flag may be set if the amplitude of the detected QRS-peak is less than two times LAT. Expressed in other word, in at least one embodiment, the minimum threshold LAT may be determined by the composite estimate signals $A_{est}$, $B_{est}$ and $C_{est}$ of the input channels $C_A$, $C_B$ and $C_C$. Using vector mathematics, in one or more embodiments, in order to relate the input channels $C_A$, $C_B$ and $C_C$ to each other, the subtraction of the composite may estimate signals from each other termed the residual value, such that $A_{est}$-$B_{est}$-$C_{est}$ theoretically may result in a value which may be equal to 0. In at least one embodiment, the subtraction of the sensed signals may yield an error that includes both inherent system noise and external uncorrelated noise present on the sensing electrodes. The amplitude of inherent system noise, in at least one embodiment, may not change. Uncorrelated noise originates locally, in at least one embodiment, may not be present at all the sensing electrodes and may be associated with muscle potentials or sensing electrode rubbing. According to one or more embodiments, the error may be used to dynamically determine the minimum threshold LAT and may be derived from the three composite estimate signals $A_{est}$, $B_{est}$ and $C_{est}$ as described above, wherein $\epsilon$ is equal to an error signal resulting from the subtraction of the three composite estimate signals $A_{est}$, $B_{est}$ and $C_{est}$. In at least one embodiment, the error signal $\epsilon$ may then be high-pass filtered with the same filter settings as the combined input stream SECG used for the QRS-peak detection resulting in a high-pass filtered error signal $\epsilon_{HP}$. The error signal, in at least one embodiment, may further be filtered with a moving average filter according to the following equation:

$$\varepsilon_n = \frac{1}{4}|\varepsilon_{HP}| + \frac{3}{4}\varepsilon_{n-1},$$

wherein $\epsilon_n$ is equal to the error signal of a current sample filtered with a moving average filter. Over a predetermined amount of time, in at least one embodiment of the invention, the maximum of the averaged absolute value of the error signal of a current sample filtered with a moving average filter $\epsilon_n$ is calculated according to the following equation:

$$\epsilon_{max} = \max(\epsilon_n)|_1^m,$$

wherein m is the number of samples that occur between subsequent QRS-peak detections or sense time-outs STO.

$\epsilon_{max}$ is acquired over a deterministic time period, in one or more embodiments, especially between sensed QRS-peaks or sense time-outs STO, but it may also be acquired over set time periods not related to QRS detections. In at least one embodiment, a constant multiplier k may be used to adjust the amplitude of the minimum threshold LAT, which may be necessary due to preconditioning of the combined input stream SECG. The nominal value for k, in at least one embodiment, may be set to maximize the number of Vs events while minimizing the number of low signal flags, or k may be set to a value that compensates for the decrease in amplitude due to filtering the error signal. For example, in at least one embodiment, k may be in the range of 1 to 4. In one or more embodiments, the constant k may be further limited, such that, the scaled value of $\epsilon_{max}$ may vary between a range of values appropriate for the system. In at least one embodiment of the invention, the following equation may be used in order to avoid the minimum threshold LAT from becoming too sensitive or too insensitive:

$$LAT=14 \leq k \cdot \epsilon_{max} \leq 21.$$

Because the minimum threshold LAT may be derived from the three composite estimate signals $A_{est}$, $B_{est}$, and $C_{est}$ and because it may be constantly changing, in at least one embodiment, it provides a more accurate reference to reliably classify low signals. In one or more embodiments, if the target threshold TT may be less than the minimum threshold LAT, it may be set to the minimum threshold LAT. In this way, in at least one embodiment, the adaptive threshold ATHR may be maintained above the random sensed noise. In at least one embodiment, the above calculations may occur for every sample n of the combined input stream SECG received. By way of one or more embodiments, the maximum of the averaged absolute value of the error signal of a current sample filtered with a moving average filter $\epsilon_{max}$ may be reset after each sense detection, QRS-peak detection, or sense time-out STO, such that a new $\epsilon_{max}$ may be calculated.

In at least one embodiment of the invention, noise in the combined input stream SECG may be detected in two ways: noise condition NCND from the automatic sense control unit 50 and low signal flag LSF. According to one or more embodiments, the detection of a QRS-peak with very small amplitude, indicated by an amplitude less than a multiple of LAT, may be treated as noise because it may be deemed unreliable (e.g. see FIG. 6). In at least one embodiment, the noise condition NCND may use, for example, the target threshold TT to determine a threshold crossing while the low signal flag LSF may use the minimum threshold LAT to determine a difference in the amplitude of the combined input signal SECG. In one or more embodiments, NCND may use other threshold values such as ATHR or an independent threshold that may be derived from a feature in the SECG stream. In at least one embodiment, the noise detection may use a noise condition NCND interrupt from the automatic sense control unit 50. In one or more embodiments, the noise condition NCND may be set if the combined input signal crosses the target threshold TT while the noise sense window NSW may be still active after the detection hold-off period DHP. In at least one embodiment, no new sensed event may occur until the noise sense window NSW times out.

In one or more embodiments of the invention, the low signal flag LSF may be set when the QRS-peak of a detected QRS complex may be too low to be considered reliable, which may happen if a QRS complex has a low amplitude or if noise may have caused the detection. In at least one embodiment, the low signal flag LSF may be set or cleared upon comparing the QRS-peak amplitude to the minimum threshold LAT following the peak detection window PDW.

In one or more embodiments, if the QRS-peak of the detected signal may be less than a low signal threshold, which may be equal to or less than two times the amount of the minimum threshold LAT, then the detected QRS-peak may be declared a low signal. In this way, in at least one embodiment, if noise decreases, thereby lowering the minimum threshold LAT, the QRS-peak amplitude of a valid sensed event Vs may also be allowed to decrease.

Figure 7:
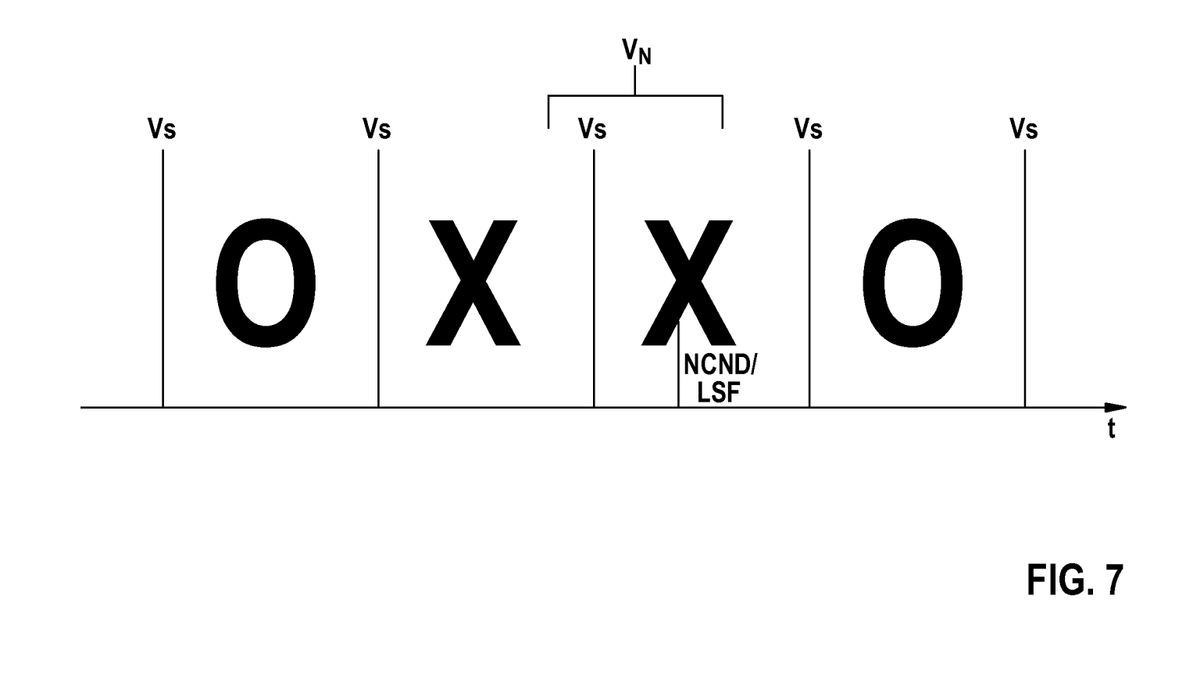
FIG. 7 shows intervals used for average cycle length calculation according to at least one embodiment of the invention.

According to one or more embodiments, the decay time of the adaptive detection threshold ATHR may be adjusted after every sensed event based on a moving average of the ventricular cycle length measured from the heart of a living being. The average cycle length ACL, in at least one embodiment, may be updated only after valid sensed events Vs are detected. FIG. 7 shows intervals used for the calculation of average cycle length ACL according to at least one embodiment of the invention. According to at least one embodiment, FIG. 7 shows a progression of sensed events, both valid and invalid (Vs and $V_N$), and it further shows which intervals may be used to calculate the average cycle length ACL. In at least one embodiment, the intervals with an "O" may be used and may be bracketed by valid sensed events Vs events, while intervals including an invalid sensed event $V_N$ may not be included, which may be indicated by an "X" in FIG. 7. Moreover, in one or more embodiments, a noise marker is shown in FIG. 7, that may indicate an invalid detection, wherein the respective intervals may not be used for the calculation of the average cycle length ACL.

As already described regarding FIG. 5, in at least one embodiment, the adaptive detection threshold ATHR may start at its maximum with a value that may be equal to a fraction of a detected QRS-peak. In one or more embodiments, the adaptive detection threshold ATHR may decay in steps until it may reach the target threshold TT. In at least one embodiment, each step may reduce the adaptive detection threshold ATHR by 12.5%. In one or more embodiments, the target threshold TT may be equal to a fraction of the same QRS-peak that may have been used for the determination of the initial value of the adaptive detection threshold ATHR. In at least one embodiment, adaptive detection threshold ATHR may not fall below the minimum threshold LAT. Furthermore, according to one or more embodiments, the maximum, initial value of the adaptive detection threshold ATHR may be equal to 87.5% of the QRS-peak detected, while the value of the target threshold TT may be equal to 25% of the QRS-peak. In at least one embodiment of the invention, the step duration of the decay of the adaptive detection threshold ATHR may be adjusted such that the adaptive detection threshold ATHR may reach 44% of the detected QRS-peak amplitude at the average cycle length ACL in time. Therefore, in at least one embodiment, as the heart rate of the heart of the living being the measurements are performed on increases or decreases, the adaptive detection threshold ATHR decays to 44% when the next QRS complex is expected. In at least one embodiment, this maintains the adaptive detection threshold ATHR above possible noise that may be present between QRS complexes, for example T-waves, muscle noise, and the like.

Figure 8:
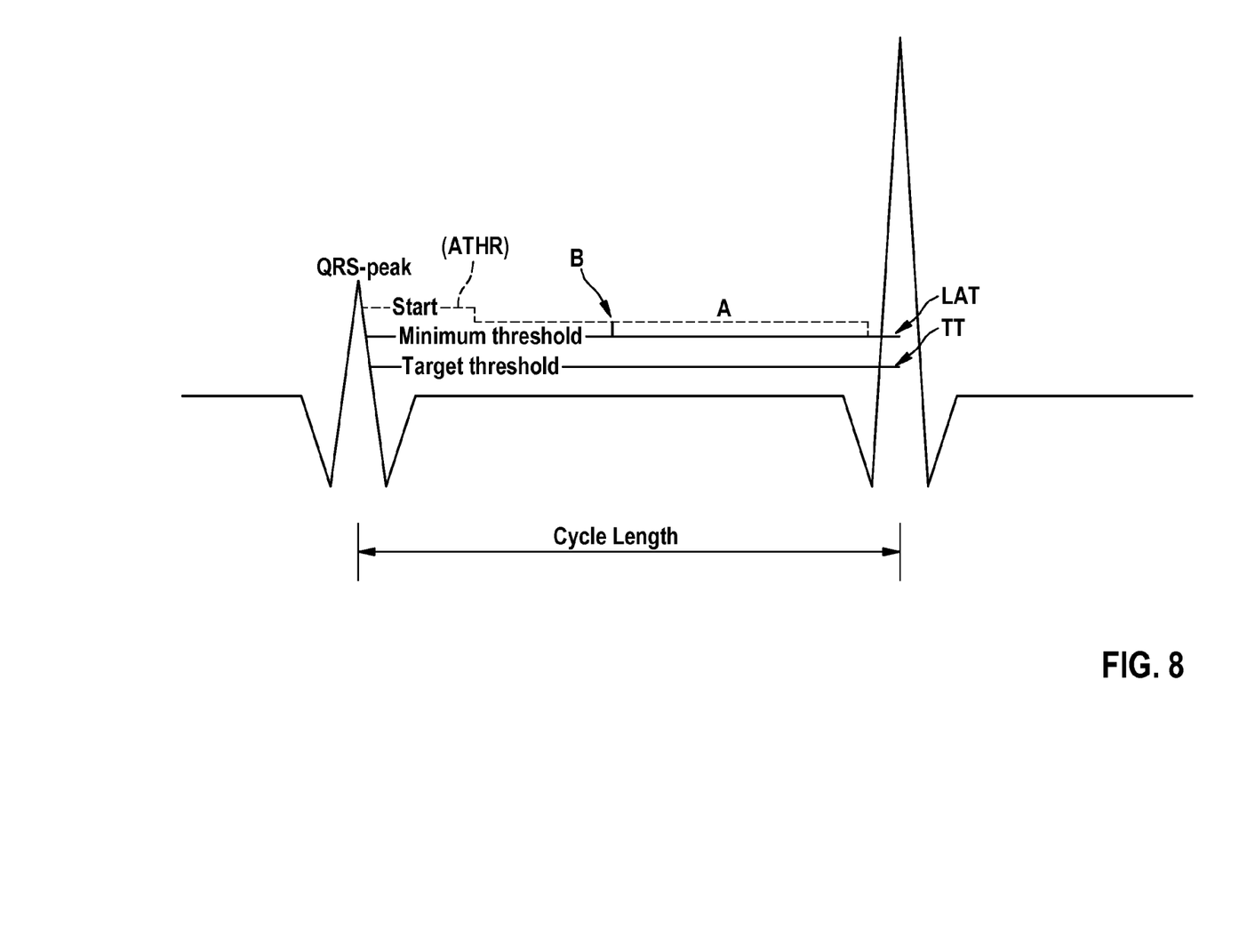
FIG. 8 shows a schematic illustration of a threshold adjustment of the adaptive detection threshold for small amplitude QRS-peaks according to at least one embodiment of the invention.

FIG. 8 shows a schematic illustration of a threshold adjustment of the adaptive detection threshold ATHR for small amplitude QRS-peaks according to at least one embodiment of the invention. In one or more embodiments, FIG. 8 shows a special situation when the amplitude of a QRS-peak may be small but may still be valid because it may not be classified as a low signal. In this case, in at least one embodiment, the estimated target threshold TT may be lower than the minimum threshold LAT if the amplitude of a detected QRS-peak may be less than four times the amount of the minimum threshold LAT, when TT may be set to 25% of the detected QRS-peak. In one or more embodiments, the adaptive detection threshold ATHR may then only decrease until it may have reached the minimum threshold LAT, which may be greater than the predicted target threshold TT, and may have caused the adaptive detection threshold ATHR to decay too rapidly to the minimum threshold LAT before the average cycle length ACL, which is shown by line B. Therefore, in by way of one or more embodiments, the time per decay step may be calculated based on the difference between the initial value of the adaptive detection threshold ATHR and the value of the minimum threshold LAT, such that the adaptive detection threshold ATHR may decay to the minimum threshold LAT at an average cycle length ACL in time, which is shown by line A. Therefore, at least one embodiment of the invention may maintain the adaptive detection threshold ATHR above possible noise while decaying fast enough to detect the next expected heart beat. In one or more embodiments, the decay of the adaptive detection threshold ATHR may adapt to changes in the heart rate and to changes in the amplitude of the QRS-peak. It should be noted that the average cycle length ACL, in at least one embodiment of the invention, does not include any intervals that include invalid sense detections, as already mentioned further above.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A method for the detection of QRS signals, comprising:
   providing at least two input heart signals via at least two separate input channels, wherein each channel is connected to pairs of external sensing electrodes, and wherein the at least two input heart signals are recorded by said pairs of external sensing electrodes and provided coincidental in time;
   generating estimated signals from the at least two input heart signals;
      wherein the estimated signals are one or more of at least one spatially derived estimate and at least one temporally derived estimate;
   combining the estimated signals to a combined input stream (SECG); and,
   detecting a QRS signal by comparing the combined input stream (SECG) to an adaptive detection threshold (ATHR) which adapts throughout time.

2. The method according to claim 1, wherein the at least one temporally derived estimate for an input channel of said at least two separate input channels comprises a smoothed value calculated from samples of the at least two input heart signals of said input channel.

3. The method according to claim 1, wherein the at least one spatially derived estimate of an input channel of said at least two separate input channels is calculated as a combination of the at least two input heart signals provided by at least a second input channel of said at least two separate input channels.

4. The method according to claim 2, wherein the step of combining the estimated signals to a combined input stream (SECG) comprises combining the at least one spatially derived estimate, the at least one temporally derived estimate and the input heart signal of an input channel for each input channel of said at least two separate input channels respectively, to provide a composite estimate signal for each input channel of said at least two separate input channels respectively.

5. The method according to claim 4, wherein the step of combining the estimated signals to a combined input stream (SECG) further comprises
   calculating a prospect for each of the at least two separate input channels respectively, using the composite estimate signals, wherein within the calculation of a certain prospect for a channel, the respective composite estimate signal calculated for the respective channel is augmented; and,
   choosing at least one prospect as the combined input stream (SECG).

6. The method according to claim 1, wherein the adaptive detection threshold (ATHR) is set after each detection of a QRS signal, wherein the value of the adaptive detection threshold (ATHR) is initially set as a percentage of a QRS-peak amplitude of the combined input stream (SECG) measured during a detection of a QRS signal, and wherein the adaptive detection threshold (ATHR) decreases throughout time.

7. The method according to claim 6, wherein the adaptive detection threshold (ATHR) decreases in steps (S) until it reaches a target threshold (TT), wherein the duration of a step (S) is adjusted based on a moving average of the ventricular cycle length measured from a composed heart signal of a body from which the combined input stream (SECG) is measured.

8. The method according to claim 7, wherein the value of the target threshold (TT) is initially set as a percentage of a QRS-peak amplitude of the combined input stream (SECG) measured during a detection of a QRS signal, and wherein the adaptive detection threshold (ATHR) and the target threshold (TT) are always greater than or equal to a minimum threshold (LAT).

9. The method according to claim 4, wherein the minimum threshold (LAT) is determined by the composite estimate signals, and wherein a vector residual of the composite estimate signals is used to determine the minimum threshold (LAT).

10. The method according to claim 7, wherein a low signal flag (LSF) is set if a detected QRS-peak amplitude of the combined input stream (SECG) is lower than a scaled value of the minimum threshold (LAT).

11. The method according to claim 1, wherein one electrode of the pairs of external sensing electrodes is shared by two of the at least two separate input channels.

12. A cardiac device (100) for use in detecting QRS signals within a composite heart signal of a body, comprising:
   an input unit (10) configured to provide at least two input heart signals via at least two separate input channels, wherein each channel is connected to pairs of external sensing electrodes, and wherein at least two input heart signals are recorded by said pairs of external sensing electrodes and provided coincidental in time;
   an estimation unit (20) configured to generate estimated signals from the at least two input heart signals;
   a combination unit configured to combine the estimated signals to a combined input stream (SECG);
   an automatic sensor control unit (50) configured compare the combined input stream (SECG) to an adaptive detection threshold (ATHR) which adapts throughout time to detect a QRS signal; and,
   a system adjustment unit (60) configured to adjust at least one parameter of le automatic sense control unit (50).

13. The cardiac device (100) according to claim 12, further comprising:
   at least one filter unit configured to filter one or more of the at least two input heart signals and the combined input stream (SECG).

14. The cardiac device according to claim 12, wherein one electrode of the pairs of external sensing electrodes is configured to be shared by two of the input channels.

15. A method for the detection of QRS signals, comprising:
   providing at least two input heart signals via at least two separate input channels, wherein each channel is connected to pairs of external sensing electrodes, and wherein the at least two input heart signals are recorded by said pairs of external sensing electrodes and provided coincidental in time;

generating estimated signals from the at least two input heart signals;

combining the estimated signals to a combined input stream (SECG); and, detecting a QRS signal by comparing the combined input stream (SECG) to an adaptive detection threshold (ATHR) which adapts throughout time;

wherein the adaptive detection threshold (ATHR) is set after each detection of a QRS signal, wherein the value of the adaptive detection threshold (ATHR) is initially set as a percentage of a QRS-peak amplitude of the combined input stream (SECG) measured during a detection of a QRS signal, and wherein the adaptive detection threshold (ATHR) decreases throughout time.

16. The method according to claim 15, wherein the adaptive detection threshold (ATHR) decreases in steps (S) until it reaches a target threshold (TT), wherein the duration of a step (S) is adjusted based on a moving average of the ventricular cycle length measured from a composed heart signal of a body from which the combined input stream (SECG) is measured.

17. The method according to claim 16, wherein the value of the target threshold (TT) is initially set as a percentage of a QRS-peak amplitude of the combined input stream (SECG) measured during a detection of a QRS signal, and wherein the adaptive detection threshold (ATHR) and the target threshold (TT) are always greater than or equal to a minimum threshold (LAT).

18. The method according to claim 16, wherein a low signal flag (LSF) is set if a detected QRS-peak amplitude of the combined input stream (SECG) is lower than a scaled value of the minimum threshold (LAT).

19. The method according to claim 15, wherein one electrode of the pairs of external sensing electrodes is shared by two of the at least two separate input channels.

20. A cardiac device (100) for use in detecting QRS signals within a composite heart signal of a body, comprising:

an input unit (10) configured to provide at least two input heart signals via at least two separate input channels, wherein each channel is connected to pairs of external sensing electrodes, and wherein at least two input heart signals are recorded by said pairs of external sensing electrodes and provided coincidental in time;

an estimation unit (20) configured to generate estimated signals from the at least two input heart signals;

a combination unit configured to combine the estimated signals to a combined input stream (SECG); and, an automatic sensor control unit (50) configured compare the combined input stream (SECG) to an adaptive detection threshold (ATHR) which adapts throughout time to detect a QRS signal.

21. The cardiac device (100) according to claim 20, further comprising:

at least one filter unit configured to filter one or more of the at least two input heart signals and the combined input stream (SECG).

22. The cardiac device according to claim 20, wherein one electrode of the pairs of external sensing electrodes is configured to be shared by two of the input channels.

* * * * *